(12) United States Patent
Schembri

(10) Patent No.: US 6,875,620 B1
(45) Date of Patent: *Apr. 5, 2005

(54) TILING PROCESS FOR CONSTRUCTING A CHEMICAL ARRAY

(75) Inventor: Carol T. Schembri, San Mateo, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/739,396

(22) Filed: Oct. 31, 1996

(51) Int. Cl.$^7$ .............. G01N 33/543; C12O 1/68; A61K 38/00; C07H 21/00

(52) U.S. Cl. .......... 436/518; 435/6; 435/DIG. 37; 435/DIG. 48; 435/DIG. 49; 530/334; 536/25.3

(58) Field of Search .............. 435/7.1, 6, DIG. 1, 435/DIG. 46, DIG. 49, DIG. 35, DIG. 37; 436/518, 536; 536/23.1, 253.3; 530/333, 334

(56) References Cited

U.S. PATENT DOCUMENTS

| | | | |
|---|---|---|---|
| 4,493,815 A | * | 1/1985 | Fernwood et al. |
| 5,143,854 A | | 9/1992 | Pirrung et al. ............... 436/518 |
| 5,265,792 A | | 11/1993 | Harrah et al. |
| 5,429,807 A | | 7/1995 | Matson et al. |
| 5,472,672 A | | 12/1995 | Brennan |
| 5,474,796 A | | 12/1995 | Brennan |
| 5,510,270 A | | 4/1996 | Fodor et al. |
| 5,545,531 A | | 8/1996 | Rava et al. ............ 435/6 |
| 5,552,270 A | | 9/1996 | Khrapko et al. |
| 5,658,754 A | * | 8/1997 | Kawasaki |
| 5,812,272 A | * | 9/1998 | King et al. ............ 356/445 |

FOREIGN PATENT DOCUMENTS

| | | | |
|---|---|---|---|
| EP | 0268237 A2 | 5/1988 | |
| EP | 0268237 B1 | 5/1988 | |
| WO | WO 94/05394 | 3/1994 | ............ B01D/25/12 |
| WO | WO 95/33846 | 12/1995 | ............ C12Q/1/100 |
| WO | WO 96/18903 | 6/1996 | ............ G01N/33/543 |

OTHER PUBLICATIONS

Webster II New Riveiside University Dictionary, pp 623–633 and 1153, Houghton Mifflin Company (1994). USA.*

Frank., Bioorganic And Med. Chem. Let. 3(3)., pp. 425–430., 1993.*

Eichler et al., Collect. Czech. Chem. Commun. vol. 54., pp. 1746–1752., 1989.*

Nicolaou K. C et al., Angew. Chem. Int. Ed. Eng. vol. 34., No. 20., pp. 2289–2291., 1995.*

Southern et al., "Arrays of Complementary Oligonucleotides for Analysing the Hybridisation Behaviour of Nucleic Acids", Nucleic Acids Research, vol. 22, No. 8, 1994, pp. 1368–1373.

Fodor et al., "Light–Directed, Spatially Addressable Parrallel Chemical Synthesis", Science, vol. 251, 1991, pp. 767–773.

Frank et al., "A New General Approach for the Simultaneous Chemical Synthesis of Large Numbers of Oligonucleotides: Segmental Solid Supports", Nucleic Acids Research, vol. 11, No. 13, 1983, pp. 4365–4377.

Bannwarth, W. and Iaiza, P., "Laboratory Methods A System for the Simultaneous Chemical Synthesis of Different DNA Fragments on Solid Support", DNA, vol. 5, No. 5, pp. 413–419, 1986.

\* cited by examiner

Primary Examiner—Padmashri Ponnaluri
(74) Attorney, Agent, or Firm—Gordon M. Stewart

(57) ABSTRACT

A process of constructing an array of chemical moieties having the following steps: forming multiple discrete physical entities (tiles) from a substantially planar material having one or more species of chemical moiety attached thereto; and picking and placing the entities (tiles) stably on a support at spatially distinct ascertainable locations to form an array of chemical moieties. The formed array includes at least two species of chemical moiety and preferably from about 50 to about 1000 species. The claimed invention includes an array formed by this process.

31 Claims, 2 Drawing Sheets

TILING PROCESS FOR CONSTRUCTING A CHEMICAL ARRAY

TECHNICAL FIELD

This invention relates generally to a process of forming an array of bioorganic molecular probes on a support, and to an array formed by this process.

BACKGROUND

Arrays of immobilized probes are currently being developed for use in assays to detect and identify components in biological samples and for screening molecular libraries. The ability to screen for multiple species of molecules in a single assay test is particularly valuable for purposes of drug discovery and clinical genetics. Accordingly, array manufacturing technologies have been developed to permit a large number of different probes to be incorporated into an array at separate and known locations (see, e.g., Fodor et al., Science 251, 767–773 (1991); Southern et al., Nucleic Acids Research 22: 1368–1373 (1994); U.S. Pat. No. 5,510,270; U.S. Pat. No. 5,474,796; U.S. Pat. No. 5,429,807; and U.S. Pat. No. 5,472,672). In these prior art methods, the probe molecules are synthesized in situ on a solid support surface at predetermined locations.

There are disadvantages to forming an array in this manner when the array is comprised of biopolymers such as oligonucleotides. The in situ method currently used for the commercial manufacture of oligonucleotide arrays is not well suited for the efficient production of arrays of long chain polymer probes because of the number of cycles of elongation required and the variable efficiency of each attachment step. For example, in order to synthesize n species of oligonucleotide having m variable positions, n×m elongation cycles are required. Although solutions have been devised to shorten the time of the overall process by segregating groups of sites for the simultaneous addition of a given nucleotide (see, e.g., Frank et al., Nucleic Acids Res. 11, 4365–4377 (1983); U.S. Pat. No. 5,510,270), manufacturing an array in this way is inefficient, particularly when the desired array is intended to include hundreds of different probe sequences and probe lengths in excess of 30 nucleotides. Each attachment step requires a finite time for covalent bond formation, and each is associated with a failure rate of between 2% and 15%. The problems with probe fidelity necessitate a high level of probe redundancy, and it is only after the entire array is formed that defects are discoverable.

Additionally, if reagents are dispensed as microdroplets, precautions must be taken to avoid intermixing of chemical moieties in neighboring droplets either by precisely depositing the droplet at its designated attachment site or by forming a pattern of differential polarities on the attachment surface to constrain the droplets to their designated attachment regions by means of surface tension.

What is needed is a process for forming an array with probes of known high fidelity in which the chemistry of attachment can be independently optimized for each different probe in the array, the density of each type of attached probe can be quantitatively assessed prior to array formation and probes not meeting specifications can be corrected or discarded prior to array assembly. The number of overall steps required to form the array is reduced in this process compared to prior art methods, and the total number of tests required to ensure the quality of manufactured arrays is equal to the number of probes in the array, not the number of arrays produced.

SUMMARY OF THE INVENTION

To address the above-mentioned need in the art, the invention disclosed and claimed herein provides a process for constructing an array of chemical moieties by forming multiple tiles comprised of a substantially planar material, each tile having attached to it at least one species of chemical moiety, and picking and placing each tile stably on a support at a separate and distinct spatial location to form an array of chemical moieties. The array formed by this process includes at least two species of chemical moiety and preferably from about 50 to about 1000 species of chemical moiety. The chemical moieties are preferably bioorganic molecular probes, most preferably nucleic acids, proteins, polysaccharides, and lipids.

An objective of this invention is to increase the speed and reproducibility of the array manufacturing process by attaching probes to discrete physical entities which can be moved robotically to separate predetermined locations on a support to create the array. The attachment step is preferably carried out in a batchwise manner to optimize the linker chemistry and attachment density of each type of probe in the array independently of the assembly of the array.

A related objective is to provide means for optimizing the linker chemistry and attachment density of each type of probe in the array independently of the assembly of the array.

Yet another objective of this invention is to streamline the quality control procedure and lower the cost of producing an array with a high degree of chemical complexity. The fidelity of synthesis of each probe type in the array and its density of attachment can be verified prior to tiling the array. The entire surface of a discrete physical entity can be tested prior to subdividing it into hundreds of thousands of tiles for placement into hundreds of thousands of arrays, thereby permitting the early detection and correction of manufacturing problems.

DETAILED DESCRIPTION OF THE INVENTION

Figure 1:
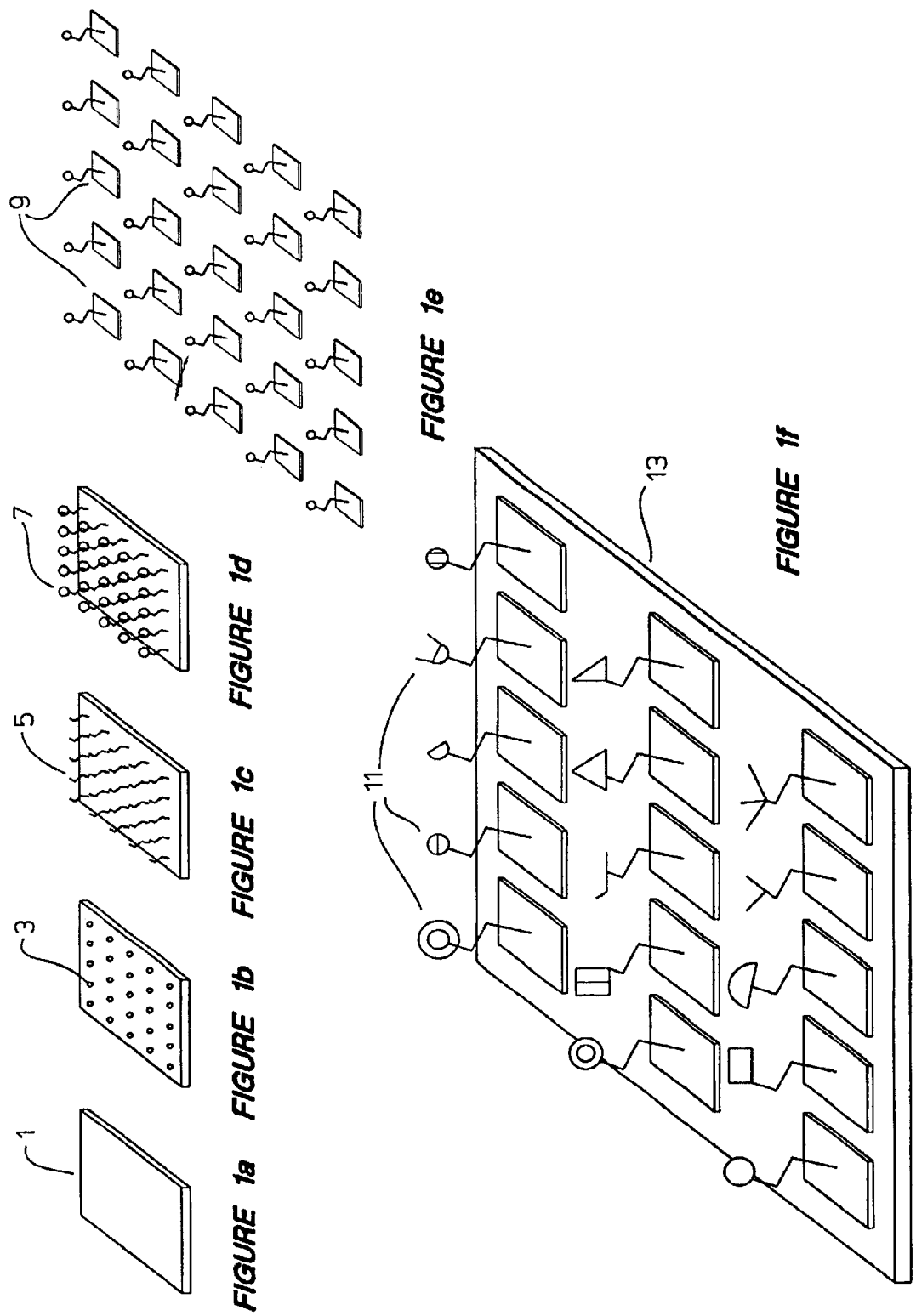
FIG. 1 illustrates schematically the steps involved in the process of forming an array of this invention.

Before the invention is described in detail, it is to be understood that this invention is not limited to the particular component parts or process steps of the methods described, as such parts and methods may vary. It is also to be understood that the terminology used herein is for purposes of describing particular embodiments only, and is not intended to be limiting. As used in the specification and the appended claims, the singular forms "a", "an", and "the" include plural referents unless the context clearly indicates otherwise.

In this specification and in the claims which follow, reference will be made to a number of terms which are used as defined below.

An "array" is an arrangement of objects in space in which each object occupies a separate predetermined spatial position. Each of the objects in the array of this invention comprise one or more species of chemical moiety attached to a "discrete physical entity", such that the physical location of each species is known or ascertainable. A "discrete physical entity" is a unit of substantially planar material (e.g., a solid material, a membrane, a gel or a combination of materials) that can be handled and still maintain its identity, and can be subdivided into "tiles" for recombining in various ways to form a physical array. Preferably, the tiles will have regular geometric shapes, e.g., a sector of a circle, a rectangle, and the like, with radial or linear dimensions of about 100 µm to about 10 mm, most preferably about 250 µm to about 1000 µm. The subdivision of the entity into tiles can be made either before or after attachment of the chemical moiety, and by any suitable method for cutting the entity, e.g., with a dicing saw. These methods are well-known in the art of semiconductor chip manufacture and can be optimized by one skilled in the art for the particular material selected for use in this invention.

A "support" is a surface or structure for the attachment of tiles. The "support" may be of any desired shape and size and can be fabricated from a variety of materials. The support material can be treated for biocompatibility (i.e., to protect biological samples and probes from undesired structure or activity changes upon contact with the support surface) and to reduce non-specific binding of biological materials to the support. These procedures are well-known in the art (see, e.g., Schöneich et al., Anal. Chem. 65: 67–84R (1993)). The tiles can be attached to the support by means of an adhesive, by insertion into a pocket or channel formed in the support, or by any other means that will provide a stable and secure spatial arrangement.

"Tiling" is the process of forming an array by picking and placing individual tiles comprising single or multiple species of chemical moieties on a support in a fixed spatial pattern.

A "chemical moiety" is an organic or inorganic molecule that is preformed at the time of attachment to a discrete physical moiety, in distinction to an organic molecule that is synthesized in situ on an array surface. The preferred mode of attachment is by covalent bonding, although noncovalent means of attachment or immobilization might be appropriate depending on the particular type of chemical moiety that is used. If desired, a "chemical moiety" can be covalently modified by the addition or removal of groups after the moiety is attached to a physically distinct entity.

The chemical moieties of this invention are preferably "bioorganic molecules" of natural or synthetic origin, are capable of synthesis or replication by chemical, biochemical or molecular biological methods, and are capable of interacting with biological systems, e.g., cell receptors, immune system components, growth factors, components of the extracellular matrix, DNA and RNA, and the like. The preferred bioorganic molecules for use in the arrays of this invention are "molecular probes" selected from nucleic acids (or portions thereof), proteins (or portions thereof), polysaccharides (or portions thereof), and lipids (or portions thereof), for example, oligonucleotides, peptides, oligosaccharides or lipid groups that are capable of use in molecular recognition and affinity-based binding assays (e.g., antigen-antibody, receptor-ligand, nucleic acid-protein, nucleic acid-nucleic acid, and the like). An array may contain different families of bioorganic molecule, e.g., proteins and nucleic acids, but typically will contain two or more species of the same family of molecule, e.g., two or more sequences of oligonucleotide, two or more protein antigens, two or more chemically distinct small organic molecules, and the like. An array can be formed from two species of molecule, although it is preferred that the array contain several tens to thousands of species of molecule, preferably from about 50 to about 1000 species. Each species of course can be present in multiple copies if desired. Different "species" then, include different families of bioorganic molecules as well as molecules of different sequence within the same family.

An "analyte" is a molecule whose detection is desired and which selectively or specifically binds to a molecular probe. An analyte can be the same or different type of molecule as the molecular probe to which it binds.

The steps involved in constructing an array by the process of this invention are diagrammed in FIG. 1.

Figure 2:
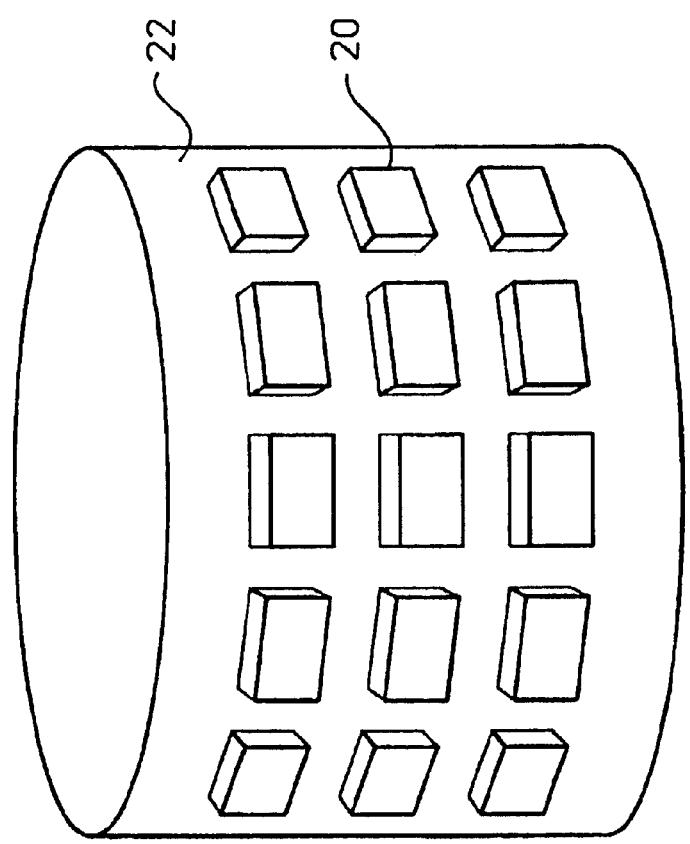
FIG. 2 illustrates an embodiment of the array in which the tiles are cylindrically arranged on a support surface.

A substantially planar "discrete physical entity" (step a, 1) is derivatized with chemically reactive groups (step b, 3). These groups are covalently attached to linker molecules (step c, 5). Of course, either or both of these steps can be bypassed if suitable functional groupings and/or linkers are inherent in the material selected for use. The linkers serve as attachment sites for chemical moieties. The linkers are contacted with a solution or droplets of chemical moieties. After binding has taken place between the linkers and chemical moieties, unreacted moieties are removed by washing. Unreacted linkers are treated so as to render them chemically inert in successive array manufacturing steps and minimize their ability to interact with analytes during subsequent assay procedures. This treatment is generically referred to herein as "capping". Thus, e.g., a reactive aldehyde or isothiocyanate group can be capped with an amine or ammonia, a reactive epoxy group can be converted with an acidic solution into a diol, and so on. In step (d), all of the linkers are shown attached to the same species of chemical moiety (7). It should be understood however that more than one species of chemical moiety may be linked to a particular entity as a matter of choice. The material is subdivided into individual tiles (step (e), 9). The subdivision can take place prior to or after step (b). In step (f), tiles comprising the same or different species of chemical moiety (shown generally at 11) are arranged on a support (13) to form an array. In an embodiment of the invention shown in FIG. 2, the tiles (20) are cylindrically arranged on a support (22). The support can be a solid rod having tiles disposed on the periphery as shown here, or the support can be a tubular structure wherein the tiles are disposed on the exterior or interior surface of the tube, or between exterior and interior surfaces, if these are spaced apart. Other variations of this shape are intended to be within the scope of this invention.

Any material can be used as a discrete physical entity, provided it is capable of subdivision into tiles, is compatible with the chemistry selected for attachment of chemical moieties to the surface, and compatible optically with detection method of the assay in which the array is to be used. Examples of suitable materials include, without limitation, glass, silicon, and plastic.

A routine method for derivatizing a glass or silicon surface for attachment of linkers is by formation of siloxane bonds, using organosilanes such as such as 3-glycidoxypropyl-trimethoxysilane ("GOPS"), 3-aminopropyltriethoxysilane (APS), and the like, which have well-understood chemistries. The linker molecule may be a bifunctional reagent that covalently binds the surface to one group and the chemical moiety to the other. Alternatively, the linker may be a reagent that is bound to the surface covalently (e.g., streptavidin) and to the molecule of interest by a high affinity noncovalent interaction (e.g., biotin). Methods for covalently linking chemical moieties to various materials for use in affinity purification procedures are well-known. See, generally, *Affinity Techniques. Enzyme Purification: Part B. Methods in Enzymology*, Vol. 34, ed. W. B. Jakoby, M. Wilchek, Acad. Press, NY (1974) and *Immobilized Biochemicals and Affinity Chromatography, Advances in Experimental Medicine and Biology*, Vol. 42, ed. R. Dunlap, Plenum Press, NY (1974). The covalent attachment of oligonucleotides to solid supports for use in hybridization assays is described in Ghosh & Musso, Nuc. Acids Res. 15: 5353–5372 (1987) and Eggers et al, Bio-Techniques 17: 516–524 (1994). Of course, the attached chemical moieties must able to interact freely with analytes in binding assays (e.g., an attached oligonucleotide must be free to hybridize to a complementary nucleic acid or to bind a sequence-specific protein, an antigen must be capable of interacting with an antibody, and so on).

The chemical moieties intended for use in the arrays of this invention are bioorganic molecules as defined above, having molecular weights in the range of about several hundreds of daltons to about several hundreds of kilodaltons. The density of molecules attached to a single physically discrete entity is intended to be in the range of about 1000 to about 100,000 molecules per square micron of surface. Various methods can be used to measure the density of molecules on monolayer surfaces. For example, the chemical moiety can be provided with a hydrolyzable group that is cleaved and measured after the moiety has attached to surface, or the chemical moiety may include labels that are directly measurable by spectrometric or microscopic techniques. These techniques and measurements are within the knowledge of one skilled in the art.

The chemical moieties are contained in a solution that can be delivered to the attachment surface of the entity in the form of droplets (see, e.g., EP 0268237 for an example of an apparatus suitable for dispensing and printing reagents) or, preferably, the solution can be held in contact with the surface. It is intended that some of the arrays formed by the process of this invention will comprise multiple arrays of chemical moieties, which can be formed in various ways. For example, an array can be printed onto a tile for placement into a tiled array. Alternatively, multiple stripes of chemical moieties, each stripe containing a unique species of chemical moiety, can be deposited on a discrete physical entity and the entity divided into multiple tiles that include each of the species at a known position on the tiles.

As noted above, the tiles can be formed in any manner appropriate to subdividing the material. Typically, the material is diced with a commercial dicing saw in the following manner. The material is placed on a thin film adhesive backing for mounting on a vacuum chuck. The dicing instrument is programmed with information about the shape of the material to be cut, the desired depth of cutting, and speed of travel of the chuck towards the blade (assuming the position of the blade is fixed). The material is cut in a first direction with a metal or diamond-impregnated blade rotating at a speed of about 20,000 rpm. Debris generated by cutting can be directed away from the cut surface with a jet of air, gas or liquid. The material is then rotated through a desired angle and cutting is continued in a second direction until the formation of tiles is completed.

The array is formed by transferring the tiles from the thin film adhesive backing (see above) to a support in a stable predetermined spatial arrangement. The transfer (herein referred to as "picking and placing") can be performed with procedures that are known in the manufacture of integrated circuits and LEDs (see, e.g., U.S. Pat. No. 5,256,792). The following automated procedure is an example of a robotics procedure that has been used to pick and place tiles comprising oligonucleotides and proteins one at a time on a support in a stable spatial arrangement. An individual tile resting on an adhesive carrier within an x-y grid was located with the aid of a camera. The tile was ejected from the underside of its adhesive backing with a needle, picked up with a vacuum probe, re-inspected with a camera, moved with an x-y planar motor to a predetermined position on a support, and inserted into a holder in the support. Preferably, the tiles are arranged in a circular pattern and held in place by grooved channels formed within the support, rather than by an adhesive. The techniques for forming microstructures such as pockets, grooves or channels capable of attaching tiles in a support are well-known in the art of microfabrication.

The arrays formed by the above-described process are intended for use in a molecular recognition-based assay, in which a sample containing an analyte whose detection is desired is brought into contact with an array of molecules of known structure or activity located at predetermined spatial positions on a support; the analyte is recognized by and selectively binds to an array molecule; and the binding is of sufficiently high affinity to permit the analyte to be retained by the array molecule until detection of the analyte has been accomplished. The selective recognition might be based on a distinguishing physicochemical characteristic of the analyte (e.g., a domain having a particular charge distribution or polarity that is capable of recognition by an array molecule), or a specific chemical feature of the analyte (e.g., a specific primary sequence in a nucleic acid, protein or polysaccharide, a secondary or higher order conformational structure, or a specific chemical group or combination of groups to form an active site). It is contemplated that the arrays formed by the process of this invention will be useful for screening chemical and molecular biological libraries for new therapeutic agents, for identifying ligands for known biological receptors and new receptors for known ligands, for identifying expressed genes, characterizing genetic polymorphisms, genotyping human populations for diagnostic and therapeutic purposes, and many other uses.

In using an array formed according to the process of this invention, the identity of a chemical moiety bound to an analyte at any particular location in the array can be determined by detecting the location of the analyte and linking this with the array's tagged file. The tagged file is a file of information wherein the identity and position of each chemical moiety in the array pertaining to the file is stored. There are various methods of linking this tagged file with the physical array. For example, the tagged file can be physically encoded on the array or its housing by means of a silicon chip, magnetic strip or bar code. Alternatively, the information identifying the array to a particular tagged file might be included on an array or its housing, with the actual file stored in the data analysis device or in a computer in communication with the device. The linking of the tagged file with the physical array would take place at the time of data analysis. Yet another way of doing this would be to store the tagged file in a device such as a disc or card that could be inserted into the data analysis device by the array user at the time the array was used in the assay.

It should be understood that the above description and examples are intended to illustrate the invention and to provide those of ordinary skill in the art with a complete disclosure and description of how to use the method of the invention, and is not intended to limit the scope of what the inventors regard as their invention. The process of forming the array can be varied in numerous insubstantial ways including changing the order in which the steps are carried out, the selection of materials used, the geometry of the array, the size and shape of the tiles, the methods of forming discrete physical entities comprising chemical moieties and subdividing these into tiles, and the method of picking, placing and immobilizing tiles on a supporting surface. Other aspects, advantages and modifications within the scope of the invention will be apparent to those skilled in the art to which the invention pertains. All of the above-mentioned patents and publications are incorporated by reference herein.

What is claimed is:

1. A process for constructing an chemical array comprising a plurality of species of bioorganic molecules in a predetermined arrangement, said process comprising the steps of:
   1) for each species of said plurality of bioorganic molecules, constructing a batch of separate tiles by:
      (a) providing a unit of a substantially planar solid material having an attachment surface;
      (b) attaching said species of bioorganic molecule onto said attachment surface; and
      (c) subdividing said unit of substantially planar material to form a plurality of separate tiles, a surface of each of said separate tiles comprising a portion of said attachment surface; and
   2) affixing separate tiles from the said batches of tiles in predetermined spatial positions on a support.

2. The process of claim 1 wherein said affixing step 2 comprises affixing said tile to said support by insertion into a pocket formed on said support.

3. The process of claim 1 wherein said affixing step (2) comprises affixing said tile to said support with an adhesive.

4. The process of claim 1 wherein said attaching step (b) comprises contacting said attachment surface of said material with a solution of said species of bioorganic molecule.

5. The process of claim 1 wherein said species of bioorganic molecule is selected from the group consisting of nucleic acids, proteins, polysaccharides and lipids.

6. The process of claim 1 wherein said array comprises from about 50 to about 1000 different species of said bioorganic molecules and wherein said bioorganic molecules are attached to said surface of each said tile at a density of about 1000 to 100,000 bioorganic molecules per square micron of said attachment surface.

7. The process of claim 1 wherein said species of bioorganic molecule is a nucleic acid or a protein.

8. The process of claim 1 wherein said subdividing step (c) is carried out prior to said attaching step (b).

9. The process of claim 1 additionally comprising:
   prior to said subdividing step (c), said unit of substantially planar material is affixed onto a backing material, whereby said separate tiles remain affixed in place on said backing material following said subdividing step (c); and
   removing the separate tiles from the backing material prior to affixing the tiles on the support.

10. The process of claim 9 wherein said backing material comprises an adhesive film.

11. The process of claim 1, further comprising, prior to said attaching step (b), a step of derivatizing said attachment surface.

12. The process of claim 1 wherein said material comprises a solid nonporous material selected from the group consisting of a glass, a silicon, and a plastic.

13. The process of claim 1 wherein said separate tiles are regularly-shaped and said surface of each said separate tile has a longest dimension from about 100 μm to about 1 mm.

14. The process of claim 1 wherein said separate tiles are regularly-shaped and said surface of each said separate tile has a longest dimension from about 250 μm to about 1 mm.

15. The process of claim 1 wherein, for each said unit of material having an attachment surface, at least one additional species of bioorganic molecule is attached onto said attachment surface.

16. The process of claim 1 wherein, for each said unit of material having an attachment surface, at least one additional species of bioorganic molecule is attached onto said attachment surface.

17. The process of claim 1 additionally comprising bringing the constructed array into contact with a same sample.

18. The process of claim 1 additionally comprising performing a quality test on the attachment surface after the attaching and prior to the subdividing.

19. The process of claim 1 additionally comprising verifying the fidelity of the bioorganic molecules on the attachment surface prior to affixing tiles from the batches onto the support.

20. The process of claim 1 additionally comprising verifying the density of attachment of the bioorganic molecules on the attachment surface prior to affixing tiles from the batches onto the support.

21. A process according to claim 1 wherein the subdividing step (c) is carried out after said attaching step (b).

22. A process for constructing a chemical array comprising a plurality of species of nucleic acids in a predetermined arrangement, said process comprising the steps of:
   1) for each species of said plurality of nucleic acids, constructing a batch of separate tiles by:
      (a) providing a unit of a substantially planar solid material having an attachment surface;
      (b) providing said species of nucleic acid onto said attachment surface so that they are attached thereto; and
      (c) subdividing said unit of substantially planar material to form a plurality of separate tiles, a surface of each of said separate tiles comprising a portion of said attachment surface; and
   2) affixing separate tiles from the said batches of tiles in predetermined spatial positions on a support.

23. A process according to claim 22 wherein the nucleic acids are oligonucleotides.

24. A process according to claim 22 wherein in step (b) the nucleic acid is presynthesized before attachment onto said surface.

25. A process according to claim 22 wherein the subdividing step (c) is carried out after said attaching step (b).

26. A process for constructing a chemical array comprising a plurality of species of proteins in a predetermined arrangement, said process comprising the steps of:
   1) for each species of said plurality of proteins, constructing a batch of separate tiles by:
      (a) providing a unit of a substantially planar solid material having an attachment surface;
      (b) providing said species of proteins onto said attachment surface so that they are attached thereto; and
      (c) subdividing said unit of substantially planar material to form a plurality of separate tiles, a surface of each of said separate tiles comprising a portion of said attachment surface; and
   2) affixing separate tiles from the said batches of tiles in predetermined spatial positions on a support.

27. A process according to claim 26 wherein in step (b) the protein is presynthesized before attachment onto said surface.

28. A process for constructing a chemical array comprising a plurality of species of peptides in a predetermined arrangement, said process comprising the steps of:
   1) for each species of said peptides, constructing a batch of separate tiles by:
      (a) providing a unit of a substantially planar solid material having an attachment surface;
      (b) providing said species of peptide onto said attachment surface so that they are attached thereto; and
      (c) subdividing said unit of substantially planar material to form a plurality of separate tiles, a surface of each of said separate tiles comprising a portion of said attachment surface; and 2) affixing separate tiles from the said batches of tiles in predetermined spatial positions on a support.

29. A process according to claim 28 wherein in step (b) the peptide is presynthesized before attachment onto said surface.

30. A process according to claim 26 wherein the subdividing step (c) is carried out after said attaching step (b).

31. A process according to claim 28 wherein the subdividing step (c) is carried out after said attaching step (b).

* * * * *